US009200982B2

(12) United States Patent
Schieke et al.

(10) Patent No.: US 9,200,982 B2
(45) Date of Patent: Dec. 1, 2015

(54) PHASED ARRAY TURBOMACHINE MONITORING SYSTEM

(71) Applicant: General Electric Company, Schenectady, NY (US)

(72) Inventors: Sascha Schieke, Simpsonville, SC (US); Vivek Venugopal Badami, Schenectady, NY (US); Achalesh Kumar Pandey, Greenville, SC (US)

(73) Assignee: General Electric Company, Schenectady, NY (US)

( * ) Notice: Subject to any disclaimer, the term of this patent is extended or adjusted under 35 U.S.C. 154(b) by 293 days.

(21) Appl. No.: 13/933,416

(22) Filed: Jul. 2, 2013

(65) Prior Publication Data

US 2015/0007641 A1    Jan. 8, 2015

(51) Int. Cl.
*G01M 15/14* (2006.01)
*G01N 29/00* (2006.01)
*G01N 29/06* (2006.01)
*G01N 29/26* (2006.01)
*G01F 1/66* (2006.01)

(52) U.S. Cl.
CPC .................. *G01M 15/14* (2013.01); *G01F 1/66* (2013.01); *G01F 1/667* (2013.01); *G01N 29/00* (2013.01); *G01N 29/0672* (2013.01); *G01N 29/262* (2013.01); *G01N 2291/02836* (2013.01); *G01N 2291/2693* (2013.01)

(58) Field of Classification Search
CPC . G01M 15/14; G01N 29/0672; G01N 29/262; G01N 2291/2693; G01N 29/00; G01N 2291/02836; G01F 1/66
USPC .................. 73/112.01, 602, 625, 626, 649
See application file for complete search history.

(56) References Cited

U.S. PATENT DOCUMENTS

| 5,031,126 | A  | * | 7/1991  | McCulloch et al. ......... 702/136 |
|-----------|----|---|---------|-------------------------------------|
| 5,831,176 | A  | * | 11/1998 | Morgenthale et al. ..... 73/861.77 |
| 6,082,198 | A  | * | 7/2000  | Sabourin et al. ................ 73/633 |
| 6,517,240 | B1 |   | 2/2003  | Herb et al.                         |
| 7,111,982 | B1 | * | 9/2006  | Swonger, Jr. ................ 374/143 |
| 7,428,842 | B2 | * | 9/2008  | Fair et al. ........................ 73/626 |
| 2008/0134791 | A1 | * | 6/2008 | Lanken Schulz et al. ...... 73/625 |
| 2011/0247417 | A1 | * | 10/2011 | Oberdoerfer et al. .......... 73/598 |
| 2013/0050680 | A1 |   | 2/2013  | Badami et al.                       |

OTHER PUBLICATIONS

Medeiros et al., "Tomographic Image Reconstruction of Fan-Beam Projections with Equidistant Detectors Using Partially Connected Neural Networks", Learning and Nonlinear Models, vol. 1, No. 2, pp. 122-130, 2003.

* cited by examiner

*Primary Examiner* — J M Saint Surin
(74) *Attorney, Agent, or Firm* — Ernest G. Cusick; Hoffman Warnick LLC (57) ABSTRACT

Various embodiments of the invention include a system having: at least one computing device connected with an array of ultrasonic probes on a gas turbomachine component, the at least one computing device configured to: instruct a first probe in the array of ultrasonic probes to transmit an ultrasonic beam to at least one additional probe in the array of ultrasonic probes; and determine a property of a medium between the first probe and the at least one additional probe based upon a time between transmission of the ultrasonic beam from the first probe and reception of the ultrasonic beam at the at least one additional probe.

18 Claims, 6 Drawing Sheets

PHASED ARRAY TURBOMACHINE MONITORING SYSTEM

FIELD OF THE INVENTION

The subject matter disclosed herein relates to turbomachine systems. More particularly, the subject matter disclosed herein relates to monitoring operating parameters of turbomachine systems, for example, gas turbomachines.

BACKGROUND OF THE INVENTION

Turbomachines, for example, gas turbomachines including gas turbines, are commonly used in power generation operations. Conventional gas turbomachines include a compressor (e.g., an axial compressor) proximate a front region, on or more combustors proximate a middle region, and a turbine proximate a rear region.

Ambient air enters the compressor, and stationary vanes along with rotating blades impart kinetic energy to the working fluid to bring it to higher-energy state. The working fluid exits the compressor and flows to the combustor, where that working fluid mixes with fuel and ignites to generate combustion gases. These combustion gases flow from the combustors through the turbine along a gas path, and in the turbine the gases expand to produce mechanical work (e.g., via rotating a shaft connected with a dynamoelectric machine).

Changes in the operating conditions of the gas turbomachine, e.g., changes in the ambient temperature, may lead to excessive temperatures in the combustor and/or reduce the efficiency of the gas turbomachine. Conventionally, gas turbomachines include (or are connected with) a control system configured to monitor various operating parameters of the gas turbomachine and adjust operation of one or more components in the gas turbomachine to achieve a desired operating parameter. The control systems conventionally employ sensors, such as temperature sensors, to determine operating parameters within the gas turbomachine. However, these conventional control systems and temperature sensors are inadequate to accurately capture the operating parameters of the gas turbomachine.

BRIEF DESCRIPTION OF THE INVENTION

Various embodiments of the invention include a system including: an array of ultrasonic probes for affixing proximate a gas turbomachine component, the array of ultrasonic probes including: a first set of probes each having an ultrasonic transducer and an ultrasonic receiver; and a second set of probes including an ultrasonic receiver, wherein the ultrasonic transducer of at least one probe in the first set of probes is configured to communicate with the ultrasonic receiver of at least one probe in the second set of probes; and a control system connected with the array of ultrasonic probes, the control system configured to: instruct the at least one probe in the first set of probes to transmit an ultrasonic beam to the at least one probe in the second set of probes; and determine a property of a medium between the at least one probe in the first set of probes and the at least one probe in the second set of probes based upon a time between transmission of the ultrasonic beam from the at least one probe in the first set of probes and reception of the ultrasonic beam by the at least one probe in the second set of probes.

A first aspect of the invention includes a system having: an array of ultrasonic probes for affixing proximate a gas turbomachine component, the array of ultrasonic probes including: a first set of probes each having an ultrasonic transducer and an ultrasonic receiver; and a second set of probes including an ultrasonic receiver, wherein the ultrasonic transducer of at least one probe in the first set of probes is configured to communicate with the ultrasonic receiver of at least one probe in the second set of probes; and a control system connected with the array of ultrasonic probes, the control system configured to: instruct the at least one probe in the first set of probes to transmit an ultrasonic beam to the at least one probe in the second set of probes; and determine a property of a medium between the at least one probe in the first set of probes and the at least one probe in the second set of probes based upon a time between transmission of the ultrasonic beam from the at least one probe in the first set of probes and reception of the ultrasonic beam by the at least one probe in the second set of probes.

A second aspect of the invention includes a system having: a gas turbomachine including a component; and an array of ultrasonic probes affixed proximate the component, the array of ultrasonic probes including: a first set of probes each having an ultrasonic transducer and an ultrasonic receiver; and a second set of probes including an ultrasonic receiver, wherein the ultrasonic transducer of at least one probe in the first set of probes is configured to communicate with the ultrasonic receiver of at least one probe in the second set of probes; and a control system connected with the array of ultrasonic probes, the control system configured to: instruct the at least one probe in the first set of probes to transmit an ultrasonic beam to the at least one probe in the second set of probes; and determine a property of a medium between the at least one probe in the first set of probes and the at least one probe in the second set of probes based upon a time between transmission of the ultrasonic beam from the at least one probe in the first set of probes and reception of the ultrasonic beam by the at least one probe in the second set of probes.

A third aspect of the invention includes a system including: at least one computing device connected with an array of ultrasonic probes on a gas turbomachine component, the at least one computing device configured to: instruct a first probe in the array of ultrasonic probes to transmit an ultrasonic beam to at least one additional probe in the array of ultrasonic probes; and determine a property of a medium between the first probe and the at least one additional probe based upon a time between transmission of the ultrasonic beam from the first probe and reception of the ultrasonic beam at the at least one additional probe.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which.

It is noted that the drawings of the invention are not necessarily to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, the subject matter disclosed herein relates to turbomachine systems. More particularly, the subject matter disclosed herein relates to measuring operating parameters of turbomachine systems, for example, gas turbomachines.

In the following description, reference is made to the accompanying drawings that form a part thereof, and in which is shown by way of illustration specific example embodiments in which the present teachings may be practiced. These embodiments are described in sufficient detail to enable those skilled in the art to practice the present teachings and it is to be understood that other embodiments may be utilized and that changes may be made without departing from the scope of the present teachings. The following description is, therefore, merely exemplary.

As described herein, changes in the operating conditions of the gas turbomachine, e.g., changes in the ambient temperature, may lead to excessive temperatures in the combustor and/or reduce the efficiency of the gas turbomachine. Conventionally, gas turbomachines include (or are connected with) a control system configured to monitor various operating parameters of the gas turbomachine and adjust operation of one or more components in the gas turbomachine to achieve a desired operating parameter. The control systems conventionally employ sensors, such as temperature sensors, to determine operating parameters within the gas turbomachine. However, these conventional control systems and temperature sensors are inadequate to accurately capture the operating parameters of the gas turbomachine.

Reducing the variation in firing temperature of a gas turbomachine's combustor allows the turbomachine to operate at a consistently higher firing temperature without damaging components in the turbomachine. For example, the inventors have determined that an example increase of two (2) degrees Fahrenheit in firing temperature can increase the power output of a turbomachine by as much as 0.15%. Additionally, accurately measuring the flow capabilities of the turbomachine can also improve its efficiency, and consequently, its power output.

Various embodiments of the invention are directed toward systems (and related computer program products and methods) utilizing a phased array configuration and ultrasonic-based computed tomography (CT) to determine a temperatures and/or flow velocities across a two-dimensional plane within a turbomachine.

The determination of temperature using ultrasound is based on the effect that the velocity of ultrasonic waves (v) varies with the changing temperature (T) of the medium in which those waves propagate. The change in ultrasonic velocity in turn depends on the change of the elastic parameters, in particular, the density ($\rho$) and Young's modulus (E), where $v=v(T)=f(E(T), \rho(T))$.

An ultrasonic instrument can determine the travel time ($t_L$) between a transmitter and a receiver. Assuming alternating values for the wave velocity (v) along the wave path, the relationship between ($t_L$) and (v) is dictated by:

$$t_L = s/v = \int_0^s \frac{1}{v(x)} dx \quad \text{(Equation 1)}$$

However, this relationship provides an average value of the velocity (v), and therefore, an average of the temperature (T) along the ray path. Conventional approaches to overcome this averaging effect have included using solid rods with circumferential grooves as ultrasonic probes. The separation between the grooves creates an echo signal, which introduces a time delay that can be measured in the return signals. This time delay allows for measurement of the temperature of the ultrasonic probe within the space between the grooves (as a function of the time delay).

While using solid rods with circumferential grooves can help to overcome the issue of averaging, those rods can be impractical for use in a gas turbomachine. In particular, the high temperature and pressure conditions within the gas turbomachine can damage the rods and release debris, and that debris can have a detrimental effect on the turbomachine.

In contrast to the herein-noted conventional approaches, various embodiments of the invention include systems for detecting a two-dimensional temperature distribution within a gas turbomachine using a phased array configuration. In various particular embodiments of the invention, the phased array can be located proximate an inlet section of a gas turbomachine, a hot gas path section of a gas turbomachine, a combustion area of a gas turbomachine, etc.

Various particular embodiments include a system. The system can include an array of ultrasonic probes for affixing proximate a gas turbomachine component. That is, in various embodiments, the array of ultrasonic probes are configured to affix to, or proximate to, a gas turbomachine component. The array of ultrasonic probes can include: a first set of probes each having an ultrasonic transducer and an ultrasonic receiver; and a second set of probes including an ultrasonic receiver. In various embodiments described herein, each of the ultrasonic probes in the array can include an ultrasonic transducer and an ultrasonic receiver. The ultrasonic transducer of at least one probe in the first set of probes is configured to communicate with the ultrasonic receiver of at least one probe in the second set of probes. The system can further include a control system connected with the array of ultrasonic probes. According to various embodiments, the control system is configured to: instruct the at least one probe in the first set of probes to transmit an ultrasonic beam to the at least one probe in the second set of probes. The control system is further configured to determine a property of a medium between the at least one probe in the first set of probes and the at least one probe in the second set of probes based upon a time between transmission of the ultrasonic beam from the at least one probe in the first set of probes and reception of the ultrasonic beam by the at least one probe in the second set of probes.

Figure 1:
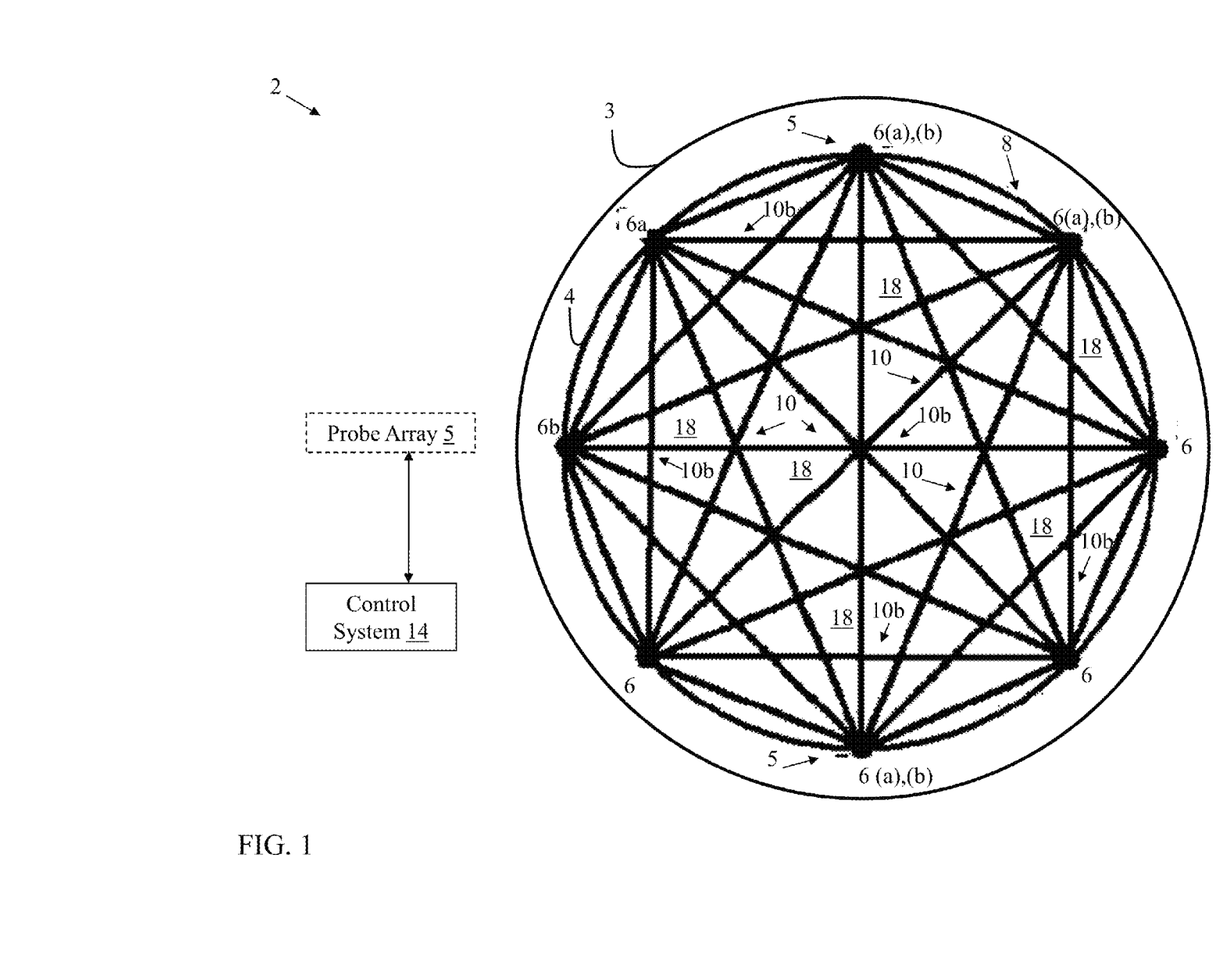
FIG. 1 shows a schematic end view of a system according to various embodiments of the invention.

FIG. 1 shows a schematic end view of a system 2, including a gas turbomachine component (e.g., a gas turbomachine inlet section) 3. The inlet section 3 can include an inlet mouth 4, and an array 5 of ultrasonic phased array probes (individually labeled) 6 affixed proximate the inlet section 3. For the purposes of clarity, each of the ultrasonic phased array probes 6 is referred to as simply an ultrasonic probe herein, however, it is understood that each ultrasonic probe 6 can include a phased array probe. Each of the ultrasonic phased array probes 6 can have its own array of transducers that can be separately pulsed according to various embodiments of the invention. As its name suggests, each ultrasonic phased array probe 6 can include a plurality (two or more) probes that can be actuated via corresponding transducers in a phased (time-delayed) manner to perform various functions described according to embodiments of the invention.

The ultrasonic probes 6 can be equally distributed along the circumference 8 of the inlet mouth 4. That is, the ultrasonic probes (or simply, probes) 6 are spaced equally along the circumference 8 of the inlet mouth 4. In various embodiments, the probes 6 in the array 5 are arranged to provide direct ultrasonic ray paths between each probe 6 and the remaining probes 6. In the example embodiment shown, where eight (8) probes 6 are illustrated in array 5, each probe 6 is configured to communicate with the remaining seven (7) probes 6, such that each probe 6 is connected with seven ultrasonic ray paths 10.

In various embodiments, a first probe 6a (or a first set of probes 6a) in the array 5 can include both an ultrasonic receiver and an ultrasonic transducer. In some cases, a second probe 6b (or a second set of probes 6b) in the array 5 can include at least an ultrasonic receiver (and in some cases an ultrasonic transducer as well). In any case, the ultrasonic transducer of the first probe 6a (and those in the first set of probes 6a) is configured to communicate with the ultrasonic receiver of the second probe 6b (and those in the second set of probes 6b). It is understood that some probes are labeled as 6, 6a, 6(a),(b), etc. merely to illustrate that any probe can act as a transmitter or receiver according to various embodiments. It is understood that in particular embodiments, all of the probes 6 in the array 5 can include the hardware and software necessary to act as a transmitter and a receiver.

As described herein, in various embodiments, the array of probes 5 is configured to mount circumferentially about the component 3. However, in other embodiments, the array of probes 5 can be configured to transmit ultrasonic beams (or ray paths) 10 in a parallel beam orientation on the gas turbomachine component 3. In this case, each probe 6 in the array of probes 5 is able to direct an ultrasonic beam 10 at only ninety-degree (perpendicular) directions. Example parallel beams are illustrated in FIG. 1 as parallel beams 10b, which are shown forming parallel vertical and horizontal pathways between probes 6, 6a, 6(a),(b) and 6.

Also shown in FIG. 1, the system 2 can further include a control system 14 connected with the array 5 of ultrasonic probes 6 (schematic connection shown). In various embodiments, the control system 14 can be connected to the array 5 via a conventional wireless or hardwired connection. In various embodiments, the control system 14 is configured to provide instructions to the ultrasonic probes 6 (e.g., transducers and/or receivers), and obtain data from the ultrasonic probes 6, e.g., when an ultrasonic receiver of a second probe 6 receives an ultrasonic beam 9 from an ultrasonic transducer in a first probe 6.

In various embodiments, the control system 14 is configured to instruct at least one probe 6a in the first set of probes 6a to transmit an ultrasonic beam 9 to at least one probe 6b in the second set of probes 6b. According to various aspects, the distance between the at least one probe 6a in the first set of probes 6a and the at least one probe 6b in the second set of probes 6b is known. In various embodiments, the distance between each of the probes 6 in the array 5 is known. As described herein, the control system 14 is configured to determine a property of a medium 18 between the at least one probe 6a in the first set of probes 6a and the at least one probe 6b in the second set of probes 6b. In some cases, the medium 18 can include a gas, such as a hot gas (e.g., a hot gas path). The property of the medium 18 can include a temperature of the medium 18, and/or a flow velocity of the medium 18.

As described herein, in various particular embodiments, the control system 14 is configured to determine the property of the medium 18 using a computed tomography (CT) analysis. That is, the control system 14 is configured to determine the property of the medium 18 by comparing the time between transmission of the ultrasonic beam 10 from the at least one probe 6a in the first set of probes 6a and reception of the ultrasonic beam 10 at the at least one probe 6b in the second set of probes 6b with a known distance between the at least one probe 6a in the first set of probes 6a and the at least one probe 6b in the second set of probes 6b.

In some particular embodiments, the control system 14 is configured to activate one probe 6 at a time as a transmitter (activating the ultrasonic transducer), and all of the remaining probes 6 in the array 5 as receivers (activating each ultrasonic receiver). The control system 14 can then actuate transmission of a plurality of ultrasonic beams 10 (e.g., substantially simultaneously or successively), where at least one of the plurality of ultrasonic beams 10 is transmitted from the transmitting probe 6 to each of the receiving probes 6 in the array. The control system 14 can then gather data from the receiving probes 6 regarding the received ultrasonic beam, for example, regarding the time-stamp for each ultrasonic beam 10 arriving at the receiving probe(s) 6 from the transmitting probe 6. As described herein, this process can be iteratively repeated for a plurality of probes 6 in the array 5, and in some cases, this process can be repeated for all of the probes 6 in the array 5, until each probe 6 has functioned as a transmitting probe and receiving probe.

Based upon the known distance between the probes 6 in the array 5, and the time required for an ultrasonic beam 10 to travel between probes 6, the control system 14 can determine an average velocity of the ultrasonic beam 9 between the transmitting probe 6 and receiving probe 6. As described herein, that average velocity of the ultrasonic beam 10 can be used to determine an average temperature of the medium 18 along the path of the ultrasonic beam 10. As shown in the example of FIG. 1, including eight probes 6 in the array 5, each probe 6 is capable of transmitting/receiving ultrasonic beams 10 to/from seven distinct probes 6. More generally, in an array of X probes, each individual probe is capable of transmitting/receiving ultrasonic beams from X−1 probes. While in some cases not all probes are configured to transmit/receive ultrasonic beams to/from other probes, the greater number of ultrasonic beams transmitted/received within an array will provide greater clarity as to the temperature (and/or flow rate) of the medium that those beams intersect. In various embodiments, the control system 14 is configured to obtain data about all of the beams (e.g., ultrasonic beams 10) transmitted/received by probes 6, and determine characteristics of the medium 18, for example, temperature, temperature gradient, temperature fluctuations, flow rate, differential flow rate, locations of turbulent and/or stagnant flow, etc.

In particular cases, the control system 14 can determine a two-dimensional distribution of temperature over a cross-section (e.g., as shown in FIG. 1) using known computed tomography (CT) algorithms. For example, the control system 14 can take all of the "views" of the cross section (where a view is equivalent to travel time, velocity, distance, etc. of a beam 10) of the component 4 and reconstruct a thermal image of the cross-section of the component 4 using at least one of: a) simultaneous linear equations; iterative techniques (e.g., Algebraic Reconstruction Technique (ART)); a Filtered Back projection; and/or a Fourier reconstruction.

Figure 2:
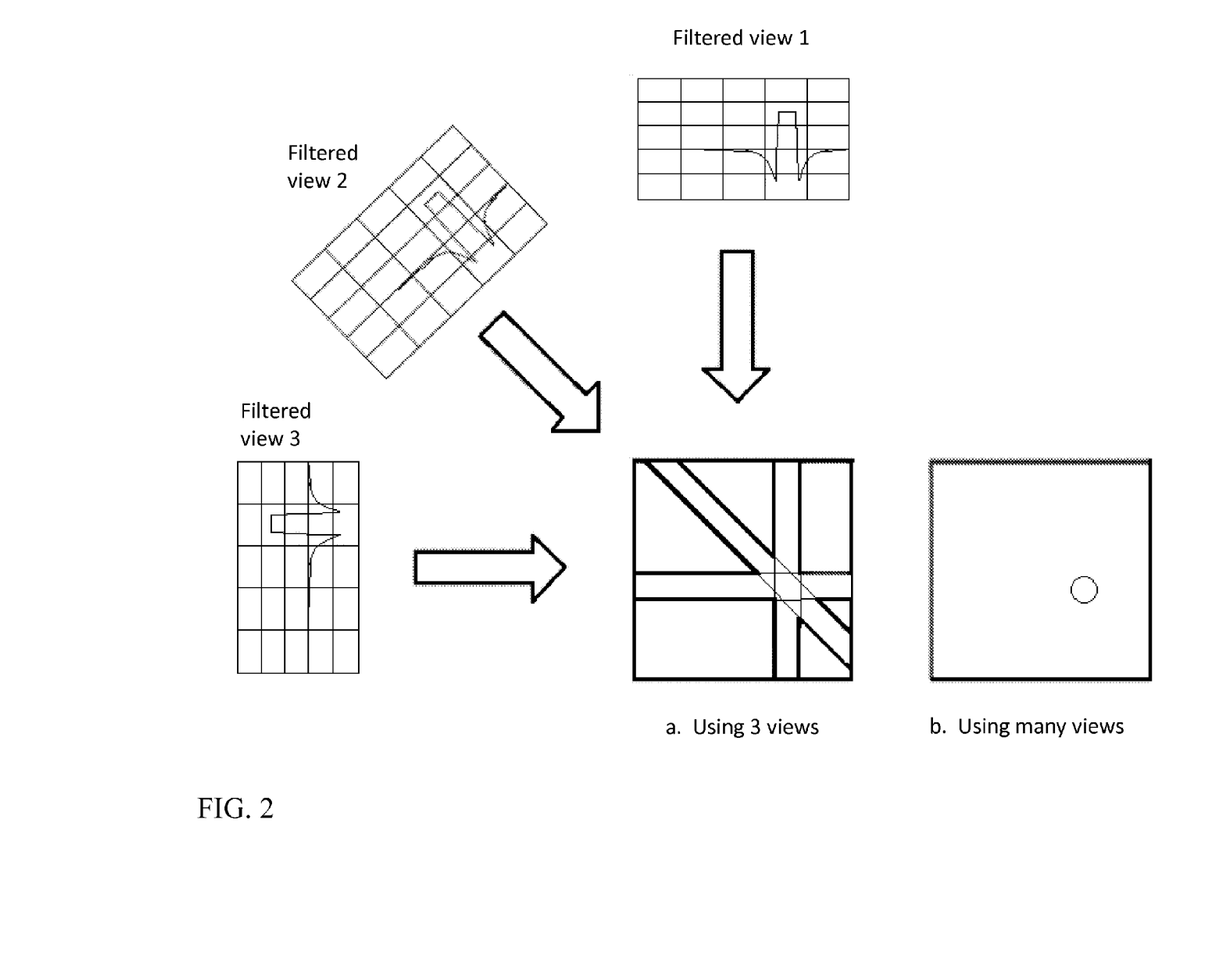
FIG. 2 shows a schematic depiction of a graphical merger of: a) three filtered views (filtered view 1, filtered view 2, filtered view 3); and b) a plurality of filtered views, according to a Filtered Back projection approach.

FIG. 2 shows a schematic depiction of a graphical merger of: a) three filtered views (filtered view 1, filtered view 2, filtered view 3); and b) a plurality of filtered views, according to the conventional Filtered Back projection approach. Using this conventional Filtered Back projection approach, an image is constructed using the distinct temperature distributions, smearing each temperature distribution along the path from which it was originally acquired. The resulting image (a) is a blurry version of the correct image.

Figure 3:
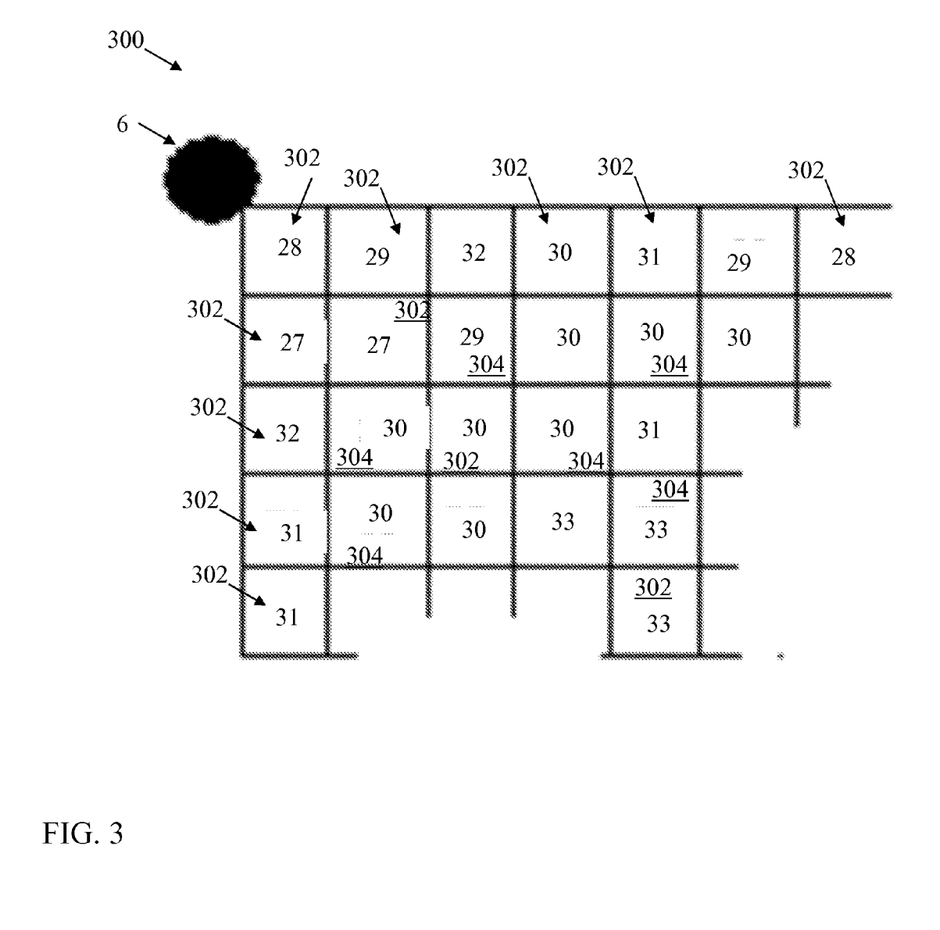
FIG. 3 shows an example temperature distribution map formed according to various embodiments of the invention.

As descried herein, and with reference to FIG. 1, increasing the number of ultrasonic transducers in an array would increase the resolution of the temperature distribution, as a greater number of ultrasonic ray paths would cover the cross-section. However, for most applications relating to gas turbomachine components (e.g., component 3), there will be gaps in the temperature distribution between each of the ultrasonic rays 10. Therefore, according to various embodiments, the control system 14 is configured to determine gaps in the temperature distribution (between rays 10) using one or more conventional averaging algorithms, for example, a 3-point, 4-point or 5-point averaging algorithm. FIG. 3 shows an example temperature distribution map 300 formed according to various embodiments, where a schematic depiction of a probe 6 is shown proximate the temperature distribution map 300. As shown, the map 300 includes values 302 obtained along a path of a ray (e.g., ray 9), and average values 304, calculated based upon the values 302 along the path of the ray (e.g., ray 9).

With continuing reference to FIG. 1, it is understood that the array 5 of probes 6 can be aligned such that at least one of the transmitting probes (e.g., first set 6a) is axially upstream of at least one of the receiving probes (e.g., second set 6b). In these cases, the array 5 can be used to detect a flow velocity of the medium 18 using these axially off-set probes (e.g., probes 6a, 6b). Conventional ultrasound techniques for detecting a flow velocity of a fluid can be used to determine the flow velocity of the medium 18. For example, the basis of the flow measurement according to various embodiments is that the ultrasonic beams can be transmitted and received both upstream (against the fluid flow) and downstream (with the fluid flow). The differential of these two travel times can then be used to determine the average flow velocity along the wave path, according to the following equation:

$$v = \frac{P^2}{2L} \frac{(t_{up} - d_{dn})}{t_{dn} \times t_{up}} \qquad \text{(Equation 2)}$$

Where v=flow velocity; ρ=distance between upstream and downstream probe along ultrasonic ray path; $t_{up}$=time ray is transmitted upstream; and $t_{dn}$=time ray is received downstream. The computed tomography (CT) algorithms used to create a two-dimensional map of the temperature of the medium 18 can also be applied to map the two-dimensional flow velocity of the medium 18.

As the velocity of ultrasonic waves is temperature-dependent, in various embodiments, the control system 14 determines the temperature conditions of the medium 18 prior to determining the flow velocity of the medium 18.

According to various embodiments, the control system 14 can modify an operating parameter of the gas turbomachine 4 in response to determining that the temperature and/or flow velocity of the medium 18 deviates from a target range. For example, the control system 14 can modify a firing temperature, fuel intake, etc. of the gas turbomachine 4 in response to determining that the temperature of the medium 18 deviates from a target temperature range. In various embodiments, the control system 14 can modify an air intake, inlet guide vane angle, etc. of the gas turbomachine 4 in response to determining that the flow velocity of the medium 18 deviates from a target flow velocity range.

Figure 4:
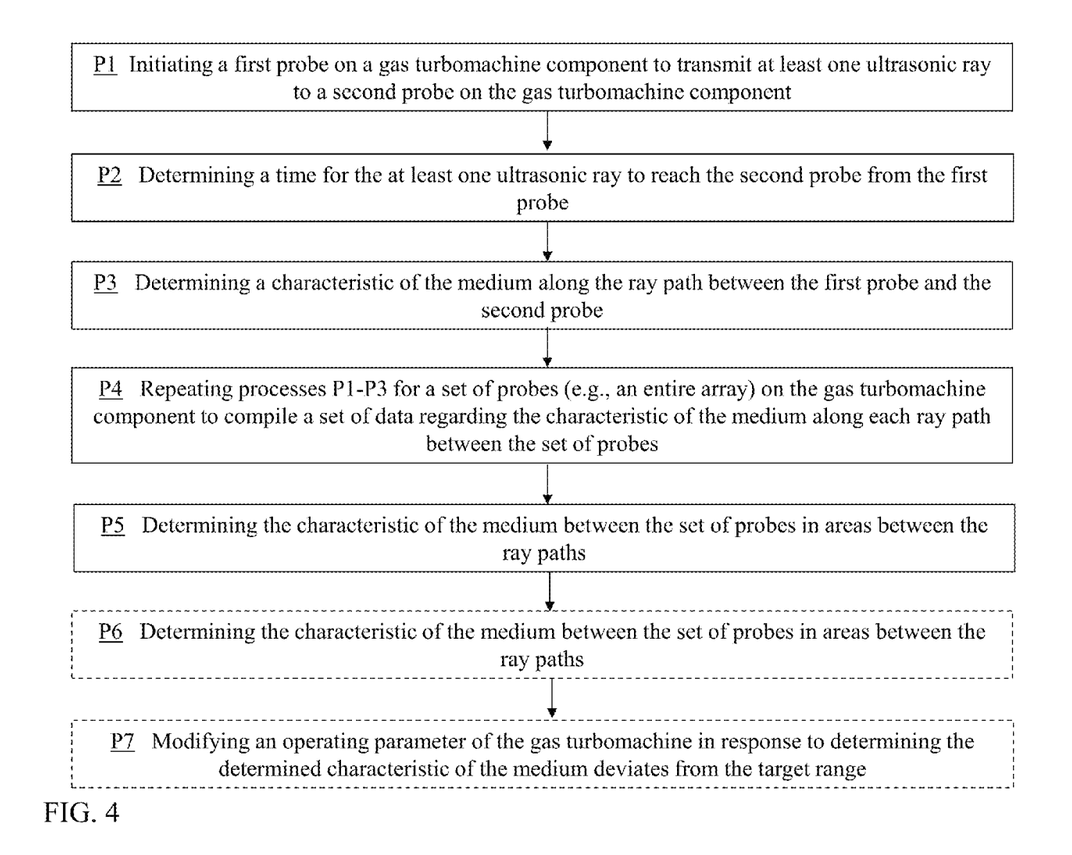
FIG. 4 is a flow diagram illustrating a process according to various embodiments of the invention.

FIG. 4 is a flow diagram illustrating a method according to various embodiments of the invention. In some cases, the method can be performed by the control system 14 or another computing device shown and/or described herein. As shown, the method can include the following processes:

P1) initiating a first probe on a gas turbomachine component to transmit at least one ultrasonic ray to a second probe on the gas turbomachine component;

P2) determining a time for the at least one ultrasonic ray to reach the second probe from the first probe;

P3) determining a characteristic (e.g., temperature, flow velocity) of the medium along the ray path between the first probe and the second probe;

P4) repeating processes P1-P3 for a set of probes (e.g., an entire array) on the gas turbomachine component to compile a set of data regarding the characteristic of the medium along each ray path between the set of probes;

P5) determining the characteristic of the medium between the set of probes in areas between the ray paths;

P6) (optionally, in some embodiments) comparing the determined characteristic of the medium with a target range for the characteristic; and P7 (optionally, in some embodiments) modifying an operating parameter of the gas turbomachine in response to determining the determined characteristic of the medium deviates from the target range.

Figure 5:
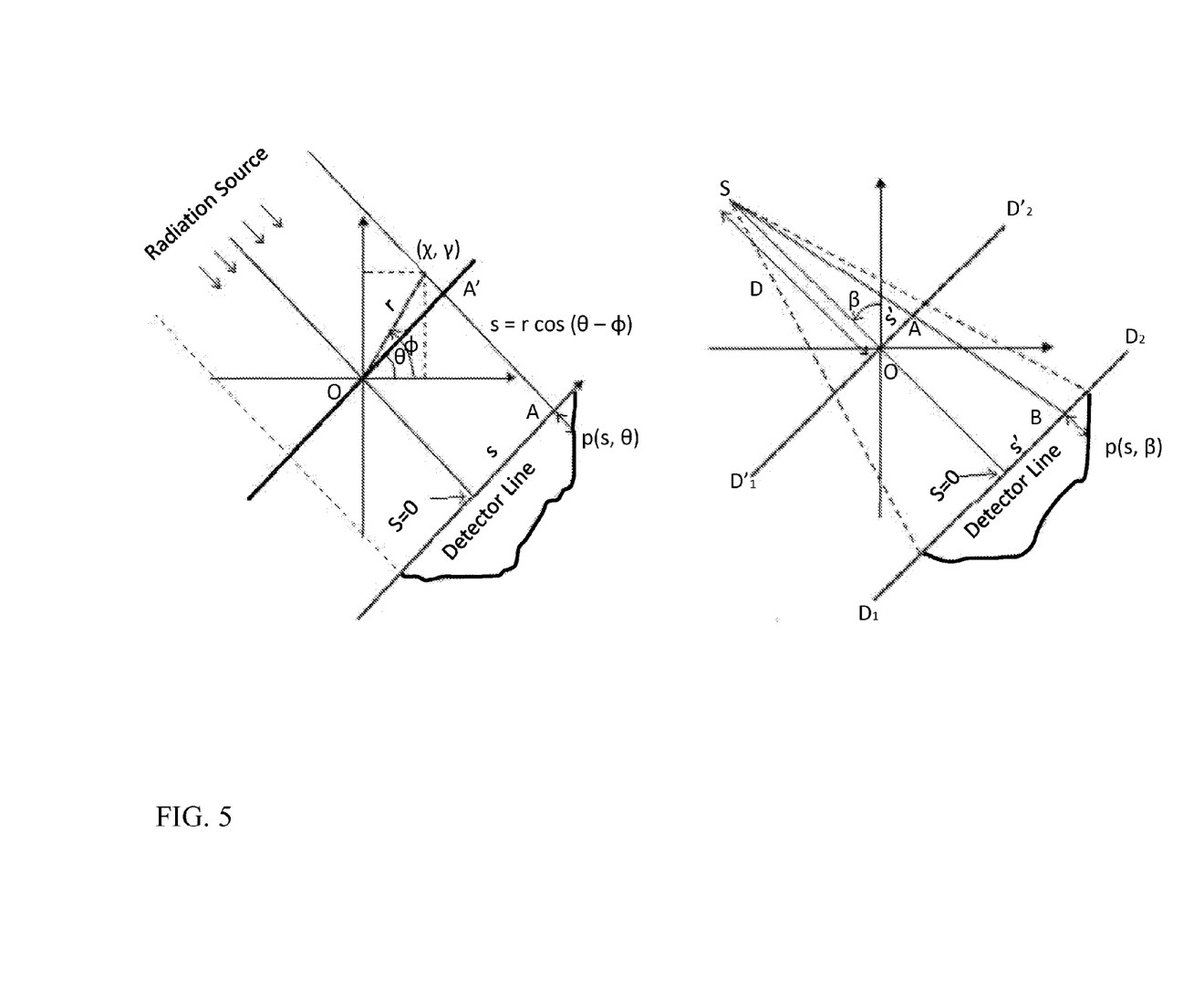
FIG. 5 shows a schematic depiction of calculating parameters used in determining a characteristic of a medium within a gas turbomachine according to various embodiments

FIG. 5 shows a schematic depiction of calculating parameters used in determining a characteristic of a medium within a gas turbomachine according to various embodiments. The left-hand depiction demonstrates a parallel beam computed tomography (CT) approach (according to various alternative embodiments described herein), and the right-hand depiction demonstrates a fan beam CT approach (according to various primary embodiments described herein).

Figure 6:
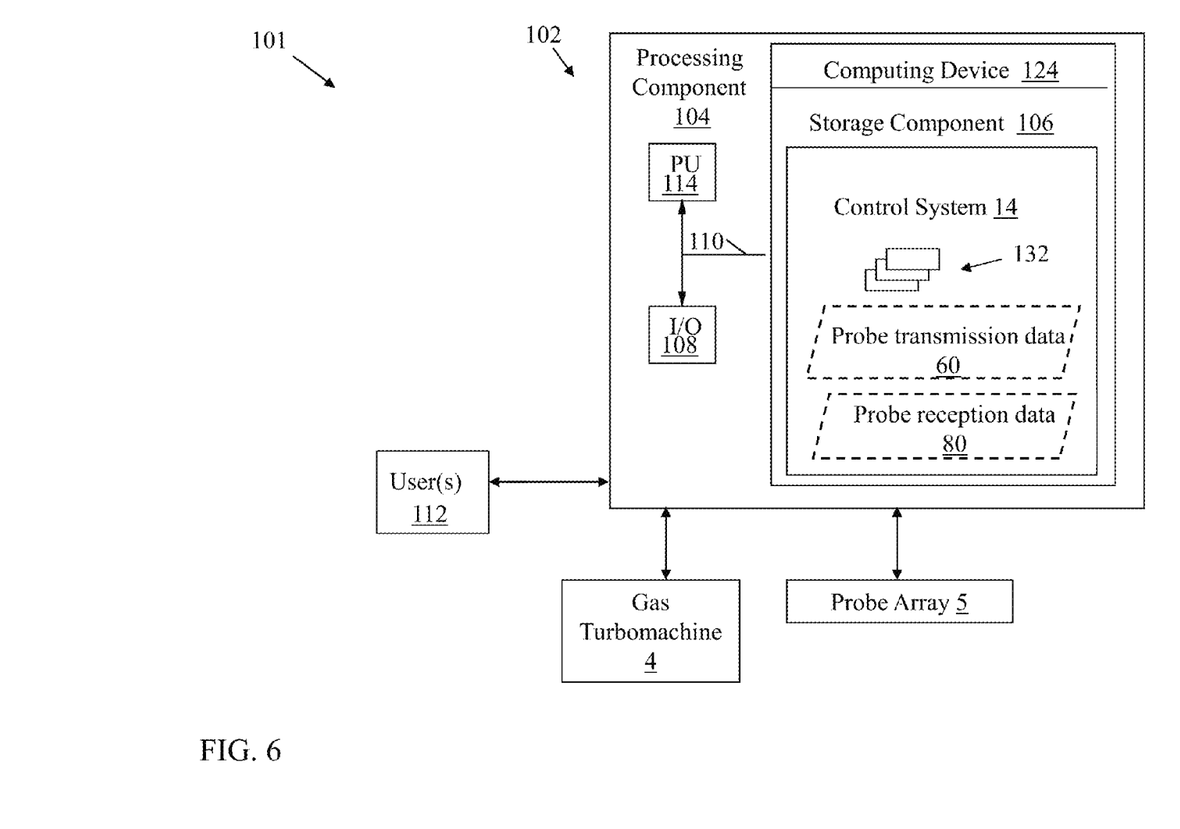
FIG. 6 shows an environment for performing various functions according to embodiments of the invention.

FIG. 6 shows an illustrative environment 101 including a control system 14, for performing the functions described herein according to various embodiments of the invention. To this extent, the environment 101 includes a computer system 102 that can perform one or more processes described herein in order to monitor a component within a turbomachine. In particular, the computer system 102 is shown as including the control system 14, which makes computer system 102 operable to monitor and/or modify an operating parameter of a gas turbomachine by performing any/all of the processes described herein and implementing any/all of the embodiments described herein.

The computer system 102 is shown including a computing device 124, which can include a processing component 104 (e.g., one or more processors), a storage component 106 (e.g., a storage hierarchy), an input/output (I/O) component 108 (e.g., one or more I/O interfaces and/or devices), and a communications pathway 110. In general, the processing component 104 executes program code, such as the control system 14, which is at least partially fixed in the storage component 106. While executing program code, the processing component 104 can process data, which can result in reading and/or writing transformed data from/to the storage component 106 and/or the I/O component 108 for further processing. The pathway 110 provides a communications link between each of the components in the computer system 102. The I/O component 108 can comprise one or more human I/O devices, which enable a user (e.g., a human and/or computerized user) 112 to interact with the computer system 102 and/or one or more communications devices to enable the system user 112 to communicate with the computer system 102 using any type of communications link. To this extent, the control system 14 can manage a set of interfaces (e.g., graphical user interface(s), application program interface, etc.) that enable human and/or system users 112 to interact with the control system 14. Further, the control system 14 can manage (e.g., store, retrieve, create, manipulate, organize, present, etc.) data, such as probe transmission data 60 and/or probe reception data 80 using any solution. The control system 14 can additionally communicate with the gas turbomachine 18 via wireless and/or hardwired means.

In any event, the computer system 102 can comprise one or more general purpose computing articles of manufacture (e.g., computing devices) capable of executing program code, such as the control system 14, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the control system 14 can be embodied as any combination of system software and/or application software. It is further understood that the control system 14 can be implemented in a cloud-based computing environment, where one or more processes are performed at distinct computing devices (e.g., a plurality of computing devices 24), where one or more of those distinct computing devices may contain only some of the components shown and described with respect to the computing device 124 of FIG. 6.

Further, the control system 14 can be implemented using a set of modules 132. In this case, a module 132 can enable the computer system 102 to perform a set of tasks used by the control system 14, and can be separately developed and/or implemented apart from other portions of the control system 14. As used herein, the term "component" means any configuration of hardware, with or without software, which implements the functionality described in conjunction therewith using any solution, while the term "module" means program code that enables the computer system 102 to implement the functionality described in conjunction therewith using any solution. When fixed in a storage component 106 of a computer system 102 that includes a processing component 104, a module is a substantial portion of a component that implements the functionality. Regardless, it is understood that two or more components, modules, and/or systems may share some/all of their respective hardware and/or software. Further, it is understood that some of the functionality discussed herein may not be implemented or additional functionality may be included as part of the computer system 102.

When the computer system 102 comprises multiple computing devices, each computing device may have only a portion of control system 14 fixed thereon (e.g., one or more modules 132). However, it is understood that the computer system 102 and control system 14 are only representative of various possible equivalent computer systems that may perform a process described herein. To this extent, in other embodiments, the functionality provided by the computer system 102 and control system 14 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 102 includes multiple computing devices 124, the computing devices can communicate over any type of communications link. Further, while performing a process described herein, the computer system 102 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

The computer system 102 can obtain or provide data, such as probe transmission data 60 and/or probe reception data 80 using any solution. The computer system 102 can generate probe transmission data 60 and/or probe reception data 80, from one or more data stores, receive probe transmission data 60 and/or probe reception data 80, from another system such as the probe array 5 and/or the user 112, send probe transmission data 60 and/or probe reception data 80 to another system, etc.

While shown and described herein as a method and system for monitoring and/or modifying an operating parameter of a gas turbomachine, it is understood that aspects of the invention further provide various alternative embodiments. For example, in one embodiment, the invention provides a computer program fixed in at least one computer-readable medium, which when executed, enables a computer system to monitor and/or modify an operating parameter of a gas turbomachine. To this extent, the computer-readable medium includes program code, such as the control system 14 (FIG. 6), which implements some or all of the processes and/or embodiments described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; etc.

In another embodiment, the invention provides a method of providing a copy of program code, such as the control system 14 (FIG. 6), which implements some or all of a process described herein. In this case, a computer system can process a copy of program code that implements some or all of a process described herein to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of program code that implements some or all of a process described herein, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of monitoring and/or modifying an operating parameter of a gas turbomachine. In this case, a computer system, such as the computer system 102 (FIG. 6), can be obtained (e.g., created, maintained, made available, etc.) and one or more components for performing a process described herein can be obtained (e.g., created, purchased, used, modified, etc.) and deployed to the computer system. To this extent, the deployment can comprise one or more of: (1) installing program code on a computing device; (2) adding one or more computing and/or I/O devices to the computer system; (3) incorporating and/or modifying the computer system to enable it to perform a process described herein; etc.

In any case, the technical effect of the various embodiments of the invention, including, e.g., the control system 14, is to monitor and/or modify an operating parameter of a gas turbomachine.

In various embodiments, components described as being "coupled" to one another can be joined along one or more interfaces. In some embodiments, these interfaces can include junctions between distinct components, and in other cases, these interfaces can include a solidly and/or integrally formed interconnection. That is, in some cases, components that are "coupled" to one another can be simultaneously formed to define a single continuous member. However, in other embodiments, these coupled components can be formed as separate members and be subsequently joined through known processes (e.g., fastening, ultrasonic welding, bonding).

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A system comprising:
an array of ultrasonic probes mounted circumferentially on a gas turbomachine component about a medium, the array of ultrasonic probes including:
a first set of probes each having an ultrasonic transducer and an ultrasonic receiver; and
a second set of probes including an ultrasonic receiver,
wherein the ultrasonic transducer of at least one probe in the first set of probes is configured to communicate with the ultrasonic receiver of at least one probe in the second set of probes; and
a control system connected with the array of ultrasonic probes, the control system configured to:
instruct the at least one probe in the first set of probes to transmit an ultrasonic beam to the at least one probe in the second set of probes; and
determine a property of the medium between the at least one probe in the first set of probes and the at least one probe in the second set of probes based upon a time between transmission of the ultrasonic beam from the at least one probe in the first set of probes and reception of the ultrasonic beam by the at least one probe in the second set of probes.

2. The system of claim 1, wherein the array of ultrasonic probes are configured to mount in a parallel beam orientation on the gas turbomachine component.

3. The system of claim 1, wherein the property of the medium includes a temperature of the medium.

4. The system of claim 1, wherein the property of the medium includes a flow velocity of the medium.

5. The system of claim 1, wherein the control system is configured to determine the property of the medium by comparing the time between transmission of the ultrasonic beam from the at least one probe in the first set of probes and reception of the ultrasonic beam at the at least one probe in the second set of probes with a known distance between the at least one probe in the first set of probes and the at least one probe in the second set of probes.

6. The system of claim 4, wherein the control system is configured to determine the property of the medium using a computed tomography (CT) analysis.

7. The system of claim 1, wherein each of the ultrasonic probes in the array of ultrasonic probes includes an ultrasonic transducer and an ultrasonic receiver.

8. A system comprising:
a gas turbomachine including a component; and
an array of ultrasonic probes mounted circumferentially on the component about a medium, the array of ultrasonic probes including:
a first set of probes each having an ultrasonic transducer and an ultrasonic receiver; and
a second set of probes including an ultrasonic receiver,
wherein the ultrasonic transducer of at least one probe in the first set of probes is configured to communicate with the ultrasonic receiver of at least one probe in the second set of probes; and
a control system connected with the array of ultrasonic probes, the control system configured to:
instruct the at least one probe in the first set of probes to transmit an ultrasonic beam to the at least one probe in the second set of probes; and
determine a property of the medium between the at least one probe in the first set of probes and the at least one probe in the second set of probes based upon a time between transmission of the ultrasonic beam from the at least one probe in the first set of probes and reception of the ultrasonic beam by the at least one probe in the second set of probes.

9. The system of claim 8, wherein the array of ultrasonic probes are configured to mount in a parallel beam orientation on the gas turbomachine component.

10. The system of claim 8, wherein the property of the medium includes a temperature of the medium.

11. The system of claim 8, wherein the property of the medium includes a flow velocity of the medium.

12. The system of claim 8, wherein the control system is configured to determine the property of the medium by comparing the time between transmission of the ultrasonic beam from the at least one probe in the first set of probes and reception of the ultrasonic beam at the at least one probe in the second set of probes with a known distance between the at least one probe in the first set of probes and the at least one probe in the second set of probes.

13. The system of claim 12, wherein the control system is configured to determine the property of the medium using a computed tomography (CT) analysis.

14. The system of claim 8, wherein the component includes an inlet section of the gas turbomachine.

15. A system comprising:
   at least one computing device connected with an array of ultrasonic probes mounted circumferentially on a gas turbomachine component about a medium, the at least one computing device configured to:
   instruct a first probe in the array of ultrasonic probes to transmit an ultrasonic beam to at least one additional probe in the array of ultrasonic probes; and
   determine a property of the medium between the first probe and the at least one additional probe based upon a time between transmission of the ultrasonic beam from the first probe and reception of the ultrasonic beam at the at least one additional probe.

16. The system of claim 15, wherein the property of the medium includes a temperature of the medium.

17. The system of claim 15, wherein the property of the medium includes a flow velocity of the medium.

18. The system of claim 15, wherein the control system is configured to determine the property of the medium by comparing the time between transmission of the ultrasonic beam from the first probe and reception of the ultrasonic beam at the at least one additional probe with a known distance between the first probe and the at least one additional probe.

* * * * *